United States Patent
Hayashi et al.

[11] Patent Number: 5,934,287
[45] Date of Patent: Aug. 10, 1999

[54] IMPLANT WITH BIOACTIVE PARTICLES STUCK AND METHOD OF MANUFACTURING THE SAME

[75] Inventors: Osamu Hayashi, Tokyo; Takamasa Sasoh, Kanagawa; Fumisada Ozawa, Saitama; Isao Furuta, Toyama; Toshitake Furusawa, Miyagi; Eiji Ichida, Tokyo, all of Japan

[73] Assignee: Brainbase Corporation, Tokyo, Japan

[21] Appl. No.: 09/106,070

[22] Filed: Jun. 29, 1998

Related U.S. Application Data

[62] Division of application No. 08/940,992, Sep. 30, 1997.

[30] Foreign Application Priority Data

| Sep. 30, 1996 | [JP] | Japan | 8-276969 |
| Jan. 29, 1997 | [JP] | Japan | 9-028266 |
| Jul. 2, 1997 | [JP] | Japan | 9-190752 |

[51] Int. Cl.⁶ ............................................. A61B 19/00
[52] U.S. Cl. ......................... 128/898; 128/897; 623/16; 623/11; 623/18; 623/66; 427/227
[58] Field of Search ................... 623/11, 16, 18, 623/66; 128/897, 898; 427/2.1, 2.24, 2.26, 2.27

[56] References Cited

U.S. PATENT DOCUMENTS

| 4,437,192 | 3/1984 | Fujiu et al. | 623/16 |
| 4,708,652 | 11/1987 | Fujiu et al. | 433/201.1 |
| 5,139,424 | 8/1992 | Yli-Urpo | 433/201.1 |
| 5,185,177 | 2/1993 | Kijima et al. | 427/2 |
| 5,251,468 | 10/1993 | Lin et al. | 72/53 |
| 5,259,398 | 11/1993 | Vrespa | 128/898 |
| 5,435,723 | 7/1995 | O'Brien | 433/174 |
| 5,505,736 | 4/1996 | Reimels et al. | 606/72 |
| 5,527,183 | 6/1996 | O'Brien | 433/174 |
| 5,549,677 | 8/1996 | Durr et al. | 623/16 |
| 5,607,480 | 3/1997 | Beaty | 623/16 |
| 5,645,934 | 7/1997 | Marcolongo et al. | 428/357 |
| 5,721,049 | 2/1998 | Marcolongo et al. | 428/370 |

*Primary Examiner*—Mickey Yu
*Assistant Examiner*—Dinh X. Nguyen
*Attorney, Agent, or Firm*—Sughrue, Mion, Zinn, Macpeak & Seas, PLLC

[57] ABSTRACT

An implant includes a main body member having biocompatibility, and particles formed of bioactive material and dispersedly provided at the surface of an embedded section of the main body member. Each of the particles has a part embedded in the embedded portion and the other part protruding from the embedded portion. The main body member is formed of titanium or titanium alloy. The particles having osteo-conduction are formed of a material selected from among a group consisting of sintered substances of hydroxylapatite, α-tricalcium phosphate, β-tricalcium phosphate, tetra-calcium phosphate, a single substance of amorphous calcium phosphate, monetite, brushite, 45S4 glass, and a mixture of them. It is desirable that the embedded section surface has a surface roughness in a range of 5 to 50 μm.

8 Claims, 10 Drawing Sheets

IMPLANT WITH BIOACTIVE PARTICLES STUCK AND METHOD OF MANUFACTURING THE SAME

This is a divisional of application Ser. No. 08/940,992 filed Sep. 30, 1997, still pending the disclosure of which is incorporated herein by reference.

BACKGROUND OF THE INVENTION

1. Field of the Invention

The present invention relates to an implant such as an implant embedded in bones and a dentistry implant and a method of manufacturing the same, and more particularly to an implant with bioactive particles stuck and a method of manufacturing the same.

2. Description of the Related Art

Titanium or titanium alloy is generally used as material of implants such as an implant embedded in bone and a dentistry implant at present. This is because when the implant is installed, the material of the implants has a state called "osteo-integration" in which the implant directly contacts bone. The osteo-integration implies the state in which there is no connective tissue between the bone and the implant. If other material is used, there is a case that the osteo-integration is not realized and a fibrous connective tissue is intervened between the implant and the bone. For this reason, the whole implant is finally covered by the fibrous connective tissue so that the fluctuation of the implant starts. Therefore, the implant must be pulled out.

In order to further increase the effect of the osteo-integration, it could be considered that the surface of the implant is made rough. There could be various methods of making the implant surface rough. For instance, as one of the methods, there is a method in which beads of metal titanium are sprayed in plasma such that the surface of the implant has many hemispheric titanium (Ti) protrusions in a microscope level and the surface area of the implant is increased. This technique also makes it possible to increase the biocompatibility of the implant with bone cells. Another method is a sand blasting method using grinding particles of alumina and so on. In this method, the surface area of the implant is increased to reflect the size of the grinding particles. Also, an anchor effect is achieved because bone enters into concave portions of the implant.

Also, the implant that a hydroxylapatite (HAP) layer is coated on the surface of the implant of titanium is commercially available. In such an implant, the connection state between the bone and the hydroxylapatite layer is called bio-integration, and it is said that the implant and the bone are chemically coupled to each other. The bio-integration is stronger than the osteo-integration in coupling strength. In a method of coating the hydroxylapatite layer, a powder of hydroxylapatite is adhered to the surface of the implant by a plasma thermal spraying method and so on. Because the hydroxylapatite layer of the implant is an aggregation of powder, the surface of the implant has portions with very small unevenness and has the above-mentioned anchor effect.

However, there are the following problems in the above-mentioned conventional implants. In the implant having the surface where the beads of titanium are sprayed in the plasma, because the plasma spraying method is the very advanced technique which requires high cost, the final implant cost becomes very expensive. On the other hand, it is possible to manufacture with low cost the implant having the surface which is subjected to the sand blasting process using the alumina grinding particles. However, there is a problem in that it is difficult to remove the adherent alumina grinding particles so that bioinert alumina particles are remained on the surface of the implant. Therefore, the formation of osteo-integration is prevented.

Further, it is in the present situation that there is little implant that the hydroxylapatite layer is coated as the commercially available products. The reason is that advanced technique is needed in the hydroxylapatite coating and it is costly. Also, the reason is that the implant having a titanium surface is finally superior to the implant having the hydroxylapatite layer, because bone coupling state is destructed through delamination of the hydroxylapatite coating layer.

SUMMARY OF THE INVENTION

In view of these points, the inventors of the present application performed various types of study and experiment as for the implant surface which had suitable roughness to bone and which could realize osteo-integration. As a result, the inventors found out a method of forming an implant having a stable surface, in which the implant had the good property of the implant having the titanium surface and the good property of the implant having the HAP coated surface. The implant can be simply manufactured from bioactive particles having osteo-conduction with low cost without bioinert impurity such as alumina particles.

Therefore, an object of the present invention is to provide an implant which has the good property of an implant having a titanium surface and the good property of an implant having a hydroxylapatite coated surface, and a method of manufacturing the same.

Another object of the present invention is to provide a method of manufacturing bioactive blasting particles.

Still another object of the present invention is to provide an implant having bioactive particles on its surface and a method of manufacturing the same.

In order to achieve an aspect of the present invention, an implant includes a main body member having bio-compatibility, and particles formed of bioactive material and dispersedly provided at a processed surface of at least a portion of the main body member such that each of the particles has a part embedded in the processed surface and a part protruding from the processed surface.

It is desirable that the processed surface has a surface roughness in a range of 5 to 50 $\mu$m, and more desirably, 15 to 30 $\mu$m. Also, it is desirable that at least a part of the processed surface includes a surface formed of one of titanium, titanium alloy and titanium oxide.

The portion corresponding to the processed surface includes a thread portion provided on the entire of the portion. In this case, the thread portion is low in height in a region near an end of the portion and is high in height in a region apart from the end of the portion. Alternatively, the portion corresponding to processed surface may include a thread portion provided in a region apart from an end of the portion.

Also, the particles have osteo-conduction. For example, the particles are formed of a material selected from among a group consisting of sintered substances of hydroxylapatite, α-tricalcium phosphate, β-tricalcium phosphate, tetra-calcium phosphate, a single substance of amorphous calcium phosphate, monetite, brushite, 45S4 glass, and a mixture of them. Each of at least particles of the particles may have a hydroxylapatite layer at the protruding part.

In order to achieve another aspect of the present invention, a method of manufacturing an implant, includes the steps of:

providing a main body member having biocompatibility; and dispersedly providing particles formed of bioactive material at a processed surface of at least a portion of the main body member such that each of the particles has a part embedded in the processed surface and a part protruding from the processed surface.

At least a part of the processed surface includes a surface formed of one of titanium and titanium alloy. Also, the particles have osteo-conduction. For example, the particles are formed of material selected from among a group consisting of sintered substances of hydroxylapatite, α-tricalcium phosphate, β-tricalcium phosphate, tetracalcium phosphate, a single substance of amorphous calcium phosphate, monetite, brushite, 45S4 glass, and a mixture of them.

The dispersion of the particles may be achieved by performing a primary sand blasting process to the processed surface using the particles. In this case, the primary sand blasting process is performed while the main body member is rotated.

In order to still another aspect of the present invention, a method of manufacturing an implant, includes the steps of:

providing a main body member having bio-compatibility;

making a processed surface of at least a portion of the main body member rough; and dispersedly providing particles formed of bioactive material at the processed surface such that each of the particles has a part embedded in the processed surface and a part protruding from the processed surface. The processed surface has a surface roughness in a range of 5 to 50 µm.

In order yet still another aspect of the present invention, a method of manufacturing an implant, includes the steps of:

providing a main body member having bio-compatibility;

dispersedly providing particles formed of bioactive material including calcium phosphate at a processed surface of at least a portion of the main body member formed of titanium or titanium alloy such that each of the particles has a part embedded in the processed surface and a part protruding from the processed surface; and forming a titanium oxide layer on the processed surface and a hydroxylapatite layer on a surface of each of the particles.

The formation titanium oxide layer may be achieved by performing hydrothermal process to the processed surface at least. In this case, a solution used in the hydrothermal process is selected from among a group consisting of pseudo-humor, suspension or saturated solution of calcium phosphate, and mixture solution of them.

The method may further include the step of performing a secondary sand blasting process to the processed surface using secondary blasting particles formed of bioactive material such that each of the secondary blasting particles has a part embedded in the processed surface and a part protruding from the processed surface.

In this case, the particles are formed from the following steps. That is, the step of forming the particles includes:

producing amorphous calcium phosphate by a precipitate method by adding phosphoric acid solution to calcium hydroxide suspension;

sintering the amorphous calcium phosphate at a predetermined temperature; and crushing the sintered amorphous calcium phosphate to select the sintered hydroxylapatite particles using a mesh.

DESCRIPTION OF THE PREFERRED EMBODIMENTS

The implant of the present invention will be described below in detail with reference to the accompanying drawings.

Figure 1B:
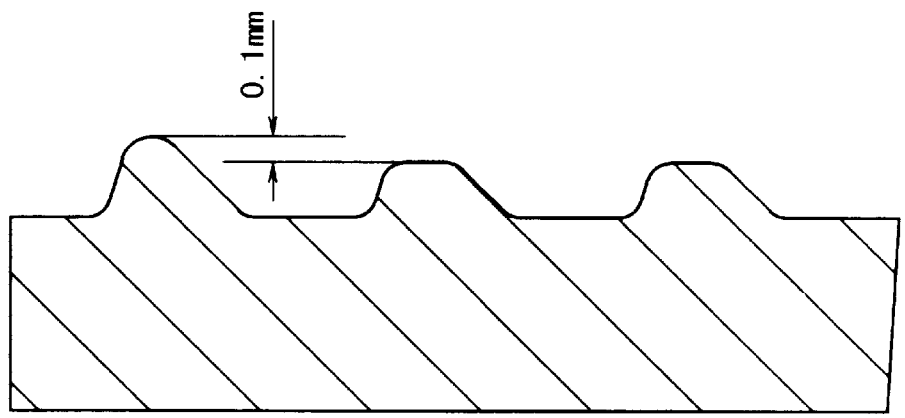
FIG. 1B is a partially expanded vertical cross sectional view of the dentistry implant shown in FIG. 2A.
Figure 1A:
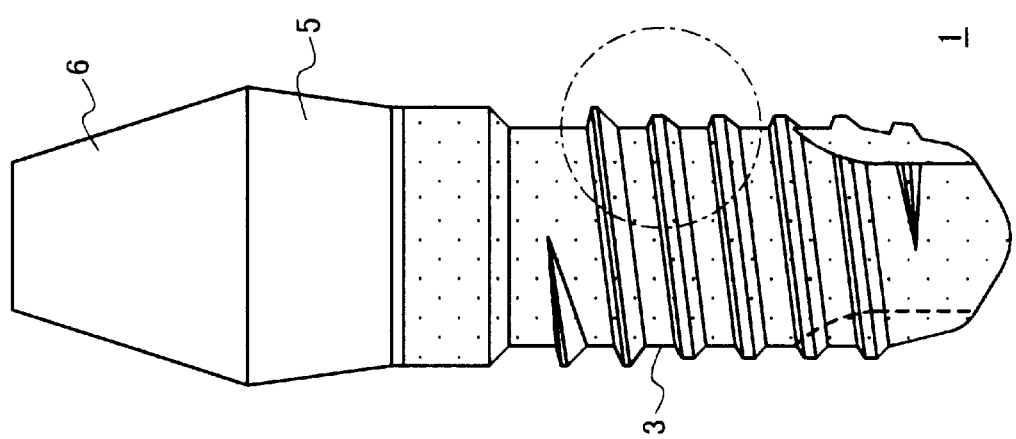
FIG. 1A is a front view of a dentistry implant according to a first embodiment of the present invention.

FIG. 1A shows the structure of a dentistry implant according to the first embodiment of the present invention. Referring to FIG. 1A, a dentistry implant 1 is formed of material having bio-compatibility such as titanium or titanium alloy. The dentistry implant 1 is composed of an embedded section 3 embedded in jawbone 2, a gingiva penetrating section 5 to be located in gingiva, and a crowned section 6 which is located on the gingiva penetrating section 5. A thread is formed on the surface of the embedded section 3. As shown in FIG. 1B, the thread of an upper portion corresponding to a cortical bone section has a triangular cross section and the thread of a lower portion corresponding to a bone marrow section has a trapezoidal cross section. Therefore, the thread of the upper portion is higher than the thread of the lower portion by a predetermined height, e.g., 0.1 mm. This height difference makes insertion of the implant easy. In this example, the heights of the thread portions are different in a step manner. However, the height of the thread may change in a continuous manner. That is, the height of the thread may be smallest in the lowermost portion and may become gradually larger toward the uppermost.

Figure 2B:
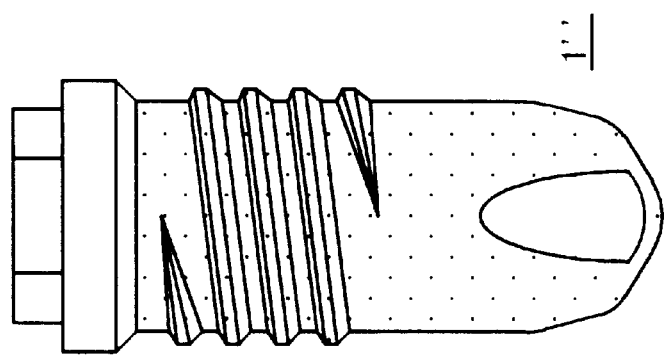
FIG. 2B is a diagram illustrating an example in which a dentistry implant according to a third embodiment of the present invention is applied.
Figure 2A:
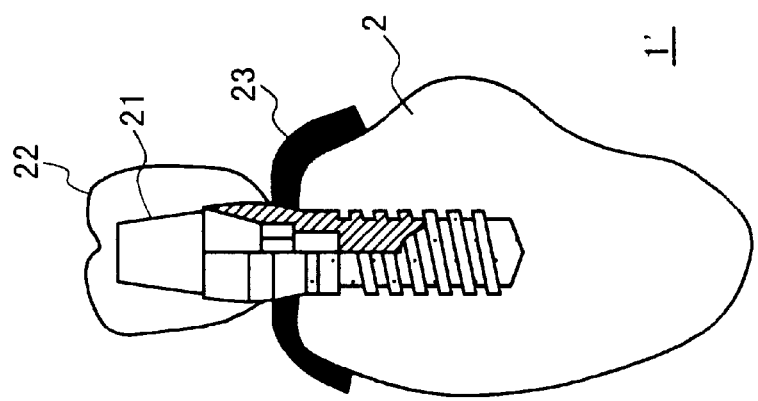
FIG. 2A is a diagram illustrating an example in which a dentistry implant according to a second embodiment of the present invention is applied.

FIG. 2A shows the structure of a dentistry implant 1' according to the second embodiment of the present invention. Referring to FIG. 2A, a dentistry implant 1' is formed of bio-compatible material such as titanium or titanium alloy, as in the first embodiment. The implant 1' is composed of an embedded section 3 embedded in jawbone 2, and a gingiva penetrating section 5 to be located in gingiva 23. There is no crowned section 6. A thread is formed on the whole surface of embedded section 3. A concave portion is formed inside of the gingiva penetrating section 5 such that an abutment 21 can be fit into the concave portion to form a crowned section 6.

FIG. 2B shows the structure of a dentistry implant 1" according to the third embodiment of the present invention. Referring to FIG. 2B, a dentistry implant is formed of bio-compatible material such as titanium or titanium alloy, as in the first embodiment. Unlike the implant shown in FIG. 2A, in the implant in the third embodiment, a thread is formed on only the upper portion of the embedded section 3 corresponding to the cortical bone section. A concave portion is formed inside of the gingiva penetrating section 5 such that an abutment 21 can be fit into the concave portion as a crowned section 6.

Figure 3:
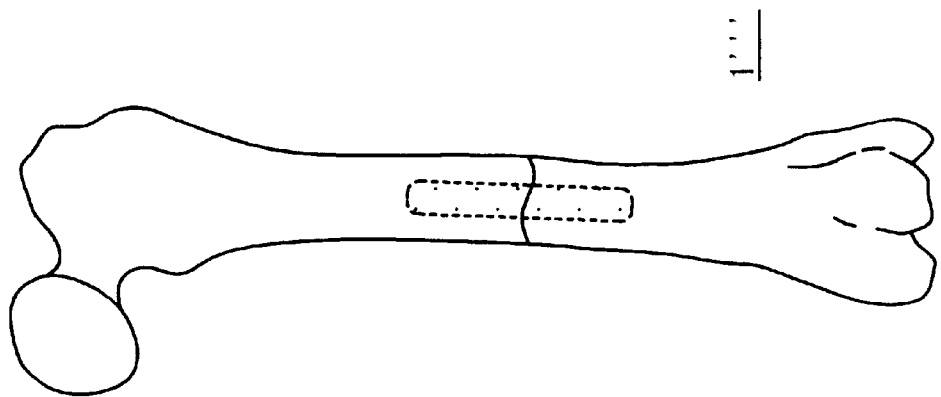
FIG. 3 is a diagram illustrating an example in which an implant according to a fourth embodiment of the present invention is applied to femur.

FIG. 3 shows a use example of an implant 1'" according to the fourth embodiment of the present invention. In this embodiment, the implant 1'" is embedded in femur sections to couple femur sections.

In the implants shown in FIGS. 1A, 2A and 2B, the whole surface of the embedded section 3 of the implant main body member as an original implant is made rough and bioactive particles having osteo-conduction are stuck on the whole surface of the embedded section 3. However, the rough surface portion with stuck particles may be formed only below the upper portion of the thread portion.

Figure 11:
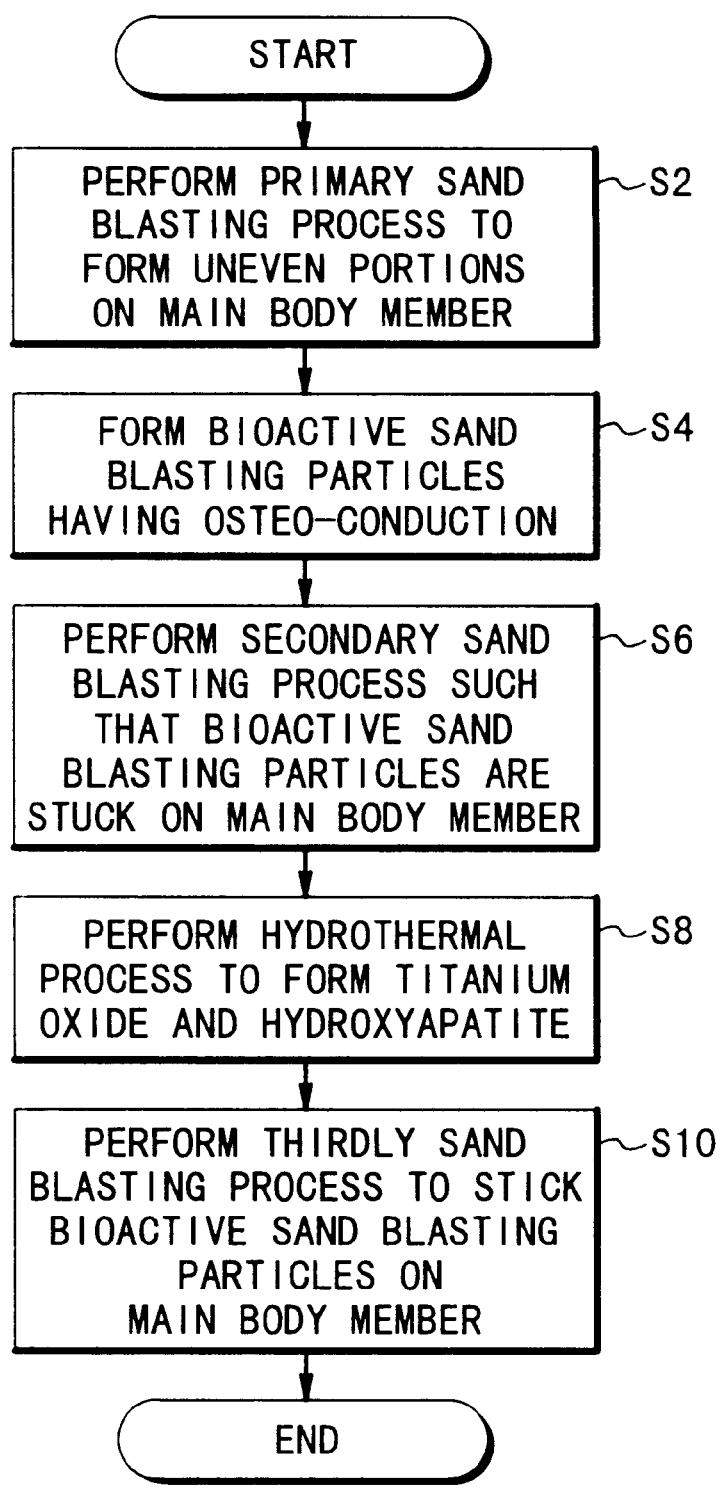
FIG. 11 is a flow chart to explain a method of manufacturing an implant of the present invention.

Referring to FIG. 11, a method of manufacturing of the implant 1 in the first embodiment will be described below.

In a step S2, the gingiva penetrating section 5 and the crowned section 6 of the main body member of titanium as an original implant 1 are masked not to be hit with grinding particles. Then, while the original implant is rotated, a primary sand blasting process is performed to the surface of the embedded section 3 of the original implant 1 using the grinding particles as the first sand blasting particles having an average grain diameter of 0.2 mm such as alumina ceramic particles, silica particles, and glass bead particles. As a result, the surface of the embedded section 3 of the original implant 1 is made rough. In this case, the roughness of the surface of the embedded section 3 is desirably in a range of 5 to 50 $\mu$m, and more desirably 15 to 50 $\mu$m, which fits to the size of osteocyte. After that, ultrasonic cleaning is performed such that the grinding particles such as alumina ceramic particles, silica particles, and glass bead particles can be physically removed as much as possible. The primary sand blasting process is very effective when the original implant 1 is formed of hard material such as titanium-nickel alloy.

Next, in a step S4, bioactive sand blasting particles are prepared before a secondary sand blasting process is performed.

When sintered hydroxylapatite particles are used as the second sand blasting particles, the sintered hydroxylapatite particles are formed in the following manner. This method is called a precipitate method. Amorphous calcium phosphate is synthesized by adding phosphoric acid solution to calcium hydroxide suspension so as to be stoichiometric to hydroxylapatite. The amorphous calcium phosphate is dehydrated, filtered and dried up at the temperature of about 120° C. After that, it is crushed by a crushing machine, and then is calcined at the temperature of about 800° C. for 1 hour. At this time, the rates of temperature increase and decrease are set to about 100° C./Hr. Next, polyvinyl alcohol aqueous solution of about 3 wt % is added to the powder which is obtained by this calcination so as to be equivalent. Further, triethylene glycol of about 1 wt % is added. Then, it is well mixed and kneaded by an automatic mortar. The mixture is dried up at the temperature of about 60° C. together with the mortar, and then fine-ground to form powder. Then, the fine-ground powder is classified using a sieve of the #200 mesh, and the classified powder under the sieve is used as granulation powder. The granulation powder obtained in this way is subjected to 1-axis formation at about 60 to 80 MPa to form a cake, and it is sintered at the temperature of about 1100° C. Finally, the sintered cake is ground and classified using #80 to 200 meshes. Thus, the sintered hydroxylapatite particles or pieces having the grain size of about 50 to 200 $\mu$m are obtained as the sand blasting particles.

Figure 4:
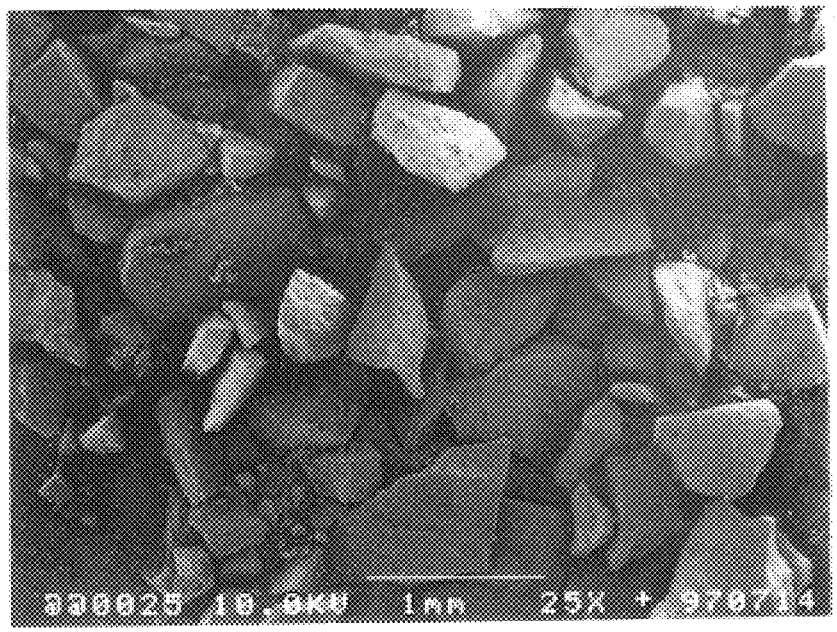
FIG. 4 is a diagram illustrating an electron microscope photograph of the surface of an implant after a sand blasting process is performed.

Alternatively, the amorphous calcium phosphate is dehydrated, filtered and dried up at the temperature of about 120° C. After that, the amorphous calcium phosphate is sintered at the temperature of about 1250° C. Finally, the sintered amorphous calcium phosphate is crushed and classified using #16 to 280 meshes. Thus, the sintered hydroxylapatite particles having the grain size of about 50 $\mu$m to 1 mm are obtained as the sand blasting particles. The sand blasting particles or pieces thus obtained are shown in an electron microscope photograph of FIG. 4.

The method of forming sintered tricalcium phosphate particles is substantially the same as the method of forming sintered hydroxylapatite (HAP) particles. However, in the step of synthesizing amorphous calcium phosphate, phosphoric acid solution is added to be stoichiometric to tricalcium phosphate. Also, if the crystal structure of target particles is $\beta$ tricalcium phosphate, the calcination temperature is set in a range of about 730 to 780° C. and the sintering temperature is set in a range of about 950 to 1130° C., for example. Preferably, the calcination temperature is set to about 750° C. and the sintering temperature is set to about 1000° C., for example. On the other hand, if the crystal structure of target particles is $\alpha$ tricalcium phosphate, the calcination temperature is set in a range of about 1100 to 1200° C. and the sintering temperature is set in a range of about 1200 to 1280° C. Preferably, the calcination temperature is set to about 1150° C. and the sintering temperature is set to about 1250° C. Finally, a sintered cake is ground and classified using #80 to 200 meshes. Thus, the sintered tricalcium phosphate particles or pieces having the grain size of about 50 to 200 $\mu$m are obtained as the sand blasting particles.

Next, in a step S6, the secondary sand blasting process is performed while the original implant 1 which is subjected to the primary sand blasting process is rotated. The secondary sand blasting process is performed using calcium phosphate ceramic particles which are smaller than the grinding particles such as alumina ceramic particles, for example, using α tricalcium phosphate ceramic particles having an average grain diameter of 0.05 to 0.2 mm. As a result, the grinding particles such as the alumina ceramic particles are removed from the surface of the original implant 1. In this case, the original implant is obtained to have the titanium surface of a surface roughness which is determined based on the primary sand blasting process and to have α-tricalcium phosphate ceramic particles remained on the titanium surface.

Figure 5:
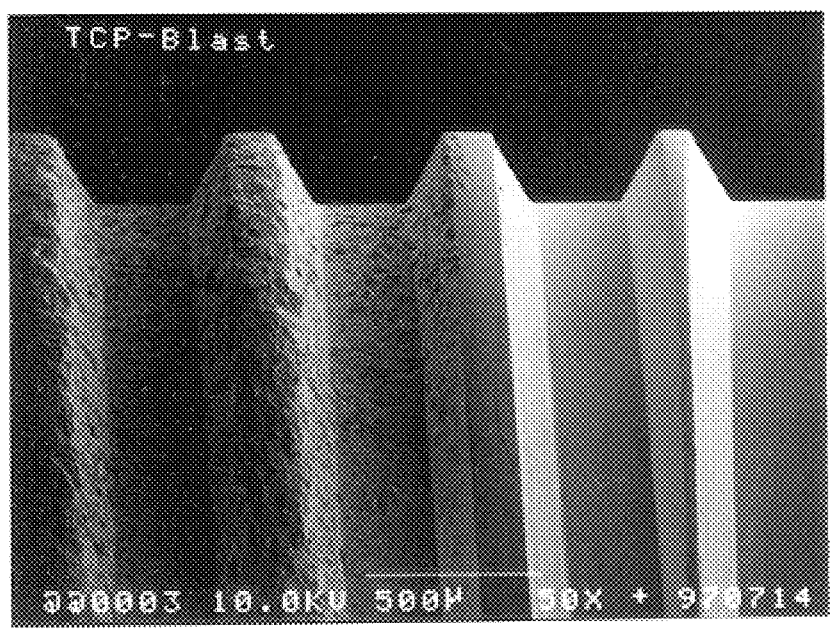
FIG. 5 is a diagram illustrating an electron microscope photograph of sand blasting particles which have osteo-conduction and which are used for the sand blasting process.

FIG. 5 shows an electron microscope photograph of the original implant 1 after the secondary sand blasting process is performed using tricalcium phosphate ceramic particles. It could be seen that the rough surface is formed on a part of the embedded section 3 of the original implant 1.

Figure 6:
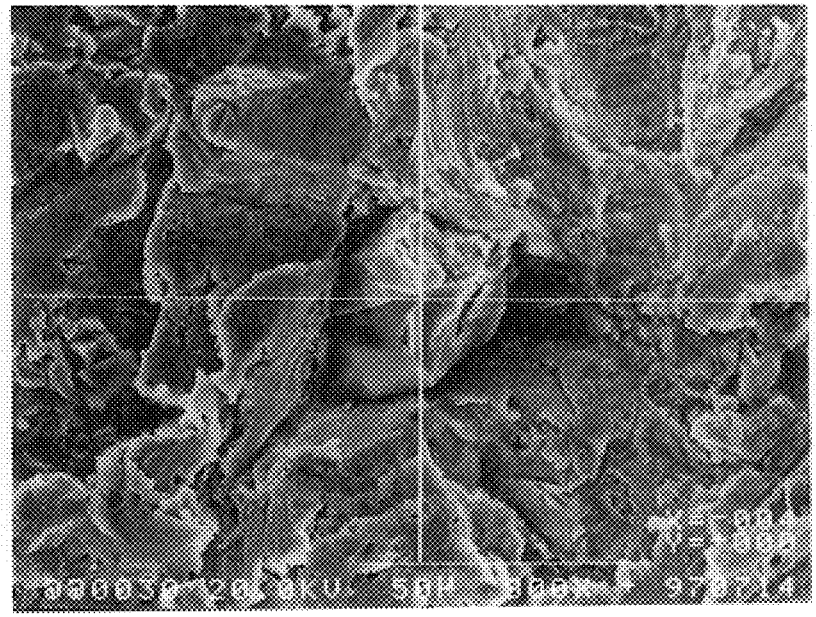
FIG. 6 is a diagram of an electron microscope photograph illustrating the state in which a sand blasting particles is stuck into a main body member as an original implant.

FIG. 6 shows an electron microscope photograph of a part of the original implant 1 after the secondary sand blasting process is performed using the sintered tricalcium phosphate ceramic particles. It is shown in the center portion that the sintered tricalcium phosphate ceramic particle is tightly coupled to the embedded section 3 of the titanium original implant 1. That is, a tip portion of the sintered tricalcium phosphate ceramic particle is stuck into the embedded section 3 and the other portion is exposed from the embedded section 3.

Figure 7:
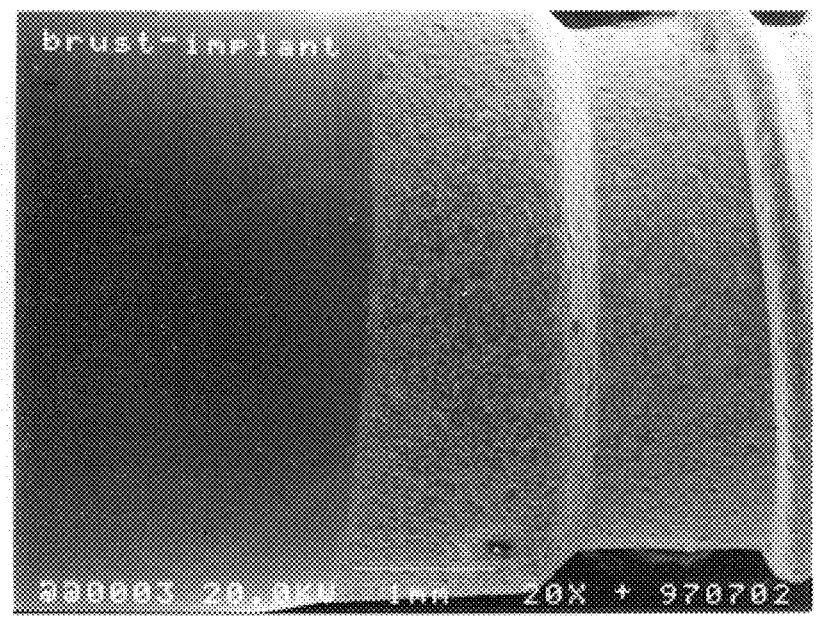
FIG. 7 is a diagram illustrating an electron microscope photograph of the surface of an implant after a sand blasting process is performed.
Figure 8:
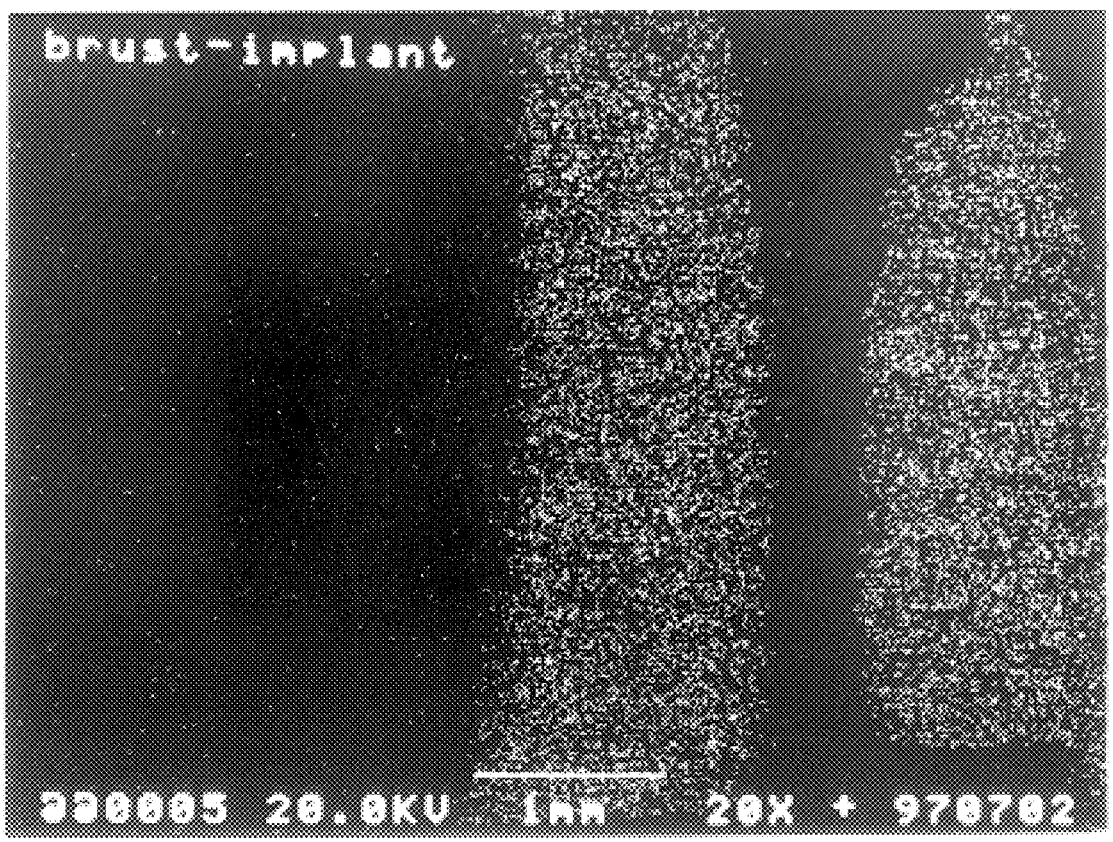
FIG. 8 is a diagram illustrating a measuring result of a portion shown in FIG. 7 by an EPMA.

FIG. 7 shows an electron microscope photograph of a part of the original implant 1 after the secondary sand blasting process is performed using the sintered tricalcium phosphate ceramic particles. FIG. 8 shows the measuring result of the part of the original implant 1 by an electron probe microanalyzer (EPMA). In FIG. 8, white dots indicate the presence of calcium. Since calcium is detected from an upper left position, there is a portion of a thread section where calcium is not detected. However, it could be seen from FIG. 8 that calcium, i.e., hydroxylapatite or calcium phosphate exists on the entire surface of the embedded section 3 of the original implant 1.

Figure 9:
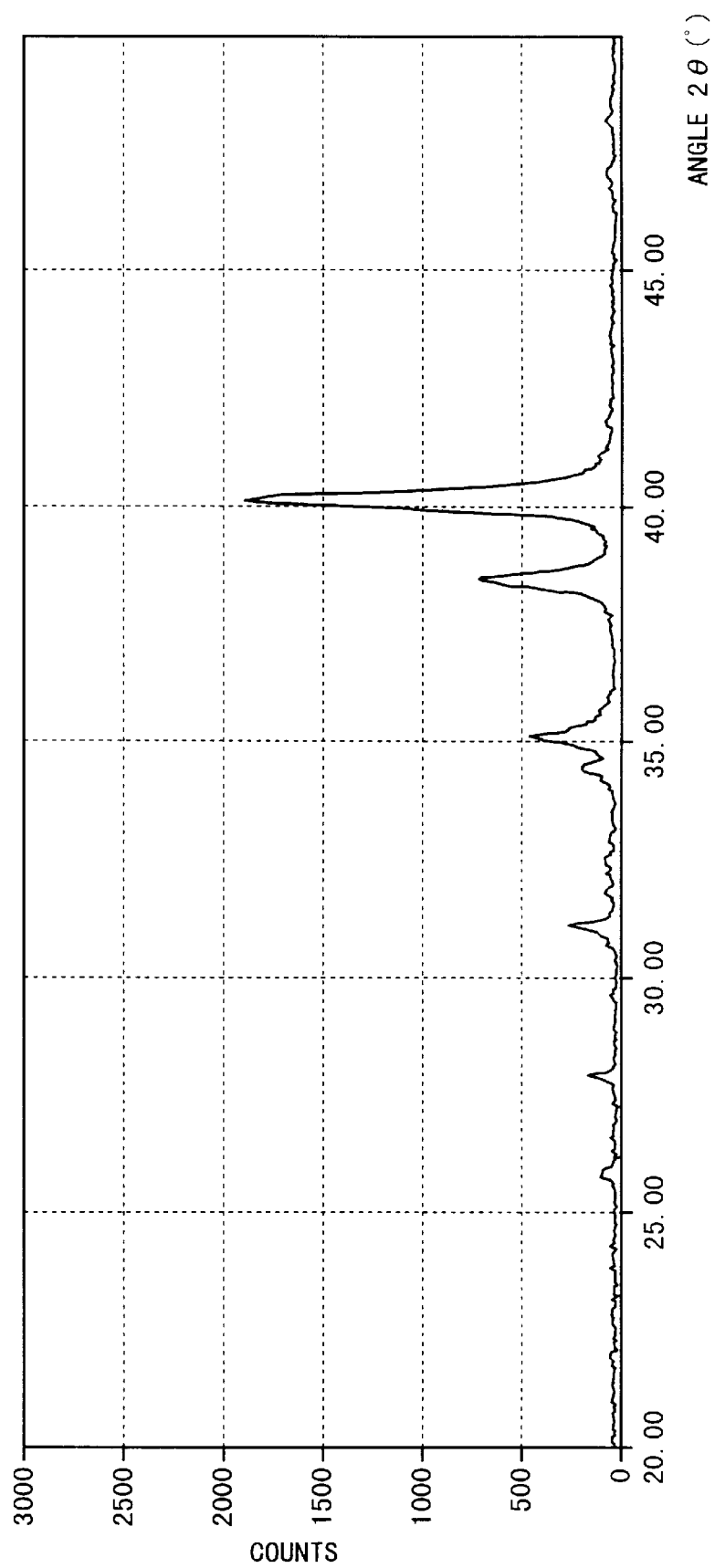
FIG. 9 is a chart obtained as a measuring result of the original implant by an X-ray diffractometer after a sand blasting process is performed using bioactive β-tricalcium phosphate (TCP) particles having a main peak at about $2\theta=31.0°$.
Figure 10:
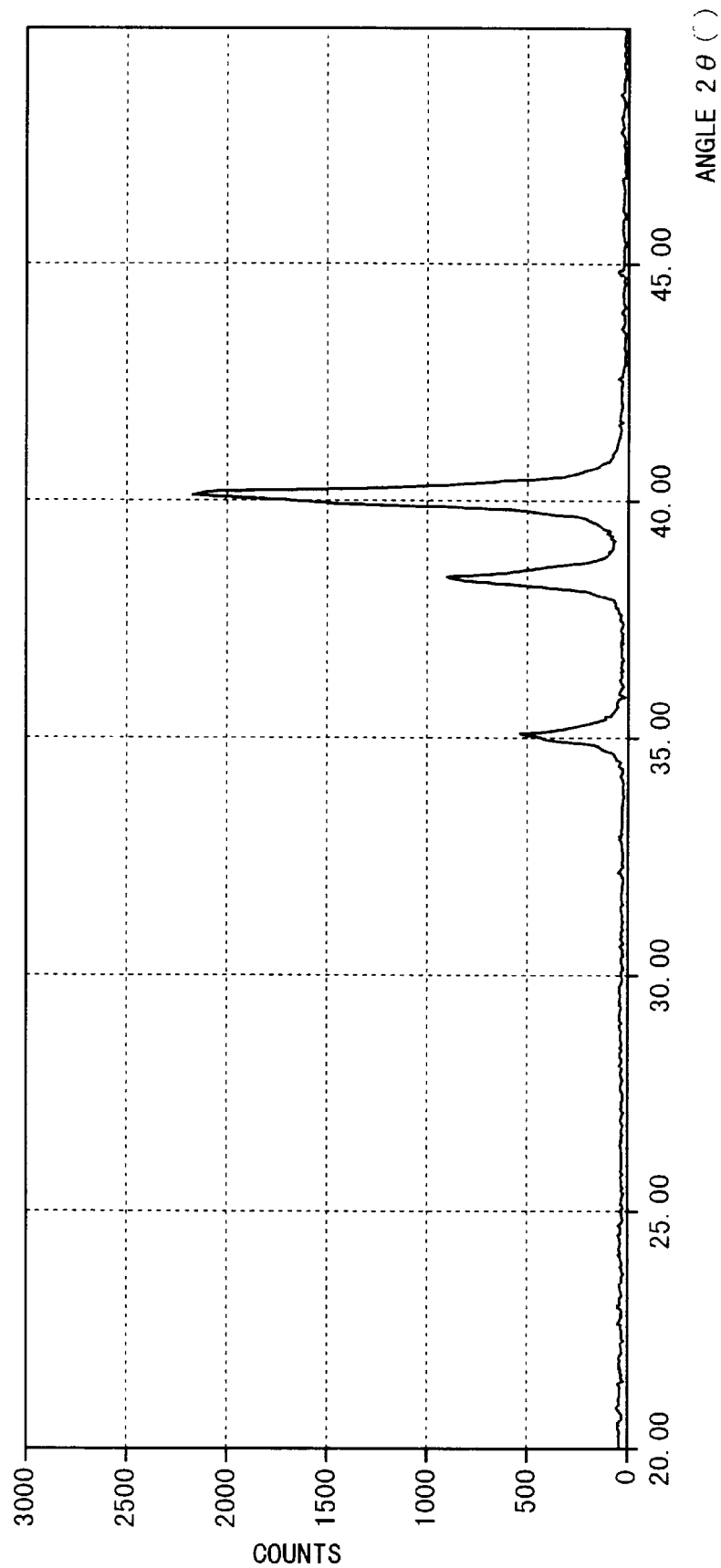
FIG. 10 is a chart obtained as a measuring result of the original implant by the X-ray diffractometer after the original implant used for the measurement shown in FIG. 9 is rinsed with 2N hydrochloric acid for one minute.

FIG. 9 shows the measuring result of the original implant 1 by an X-ray diffractometer. The original implant 1 is subjected to the secondary sand blasting process using sintered β tricalcium phosphate ceramic particles. As seen from FIG. 9, the peaks of β tricalcium phosphate appear together with peak of titanium. The calcium phosphate has the main peak at about 2θ=31 degrees. The measuring result by the X-ray diffractometer after the original implant 1 is rinsed with 2N hydrochloric acid for one minute is shown in FIG. 10. As seen from FIG. 10, the sintered β tricalcium phosphate ceramic particles dissolve and are lost.

When being blasted toward the original implant 1 to reach the surface of the original implant 1, the secondary sand blasting particles such as the sintered hydroxylapatite (HAP) ceramic particles is broken and stick into the surface of the original implant 1. As a result, a part of the broken particle is embedded into the original implant 1 and another portion protrudes from the surface of the original implant 1. These sticking fine particles are not removed by usual ultrasonic cleaning and remained on the surface. If these remained fine particles are alumina, they are recognized as bioinert material in the living body so that osteo-integration is obstructed. However, when these fine particles are hydroxylapatite (HAP) or tricalcium phosphate having high bio-activity and are formed of the material which is absorbed by bone as in the present invention, these particles have osteo-conduction to contribute the formation of bone immediately after the implantation of the complete implant and to function to help the osteo-integration.

Also, it is desirable that when the primary sand blasting process is performed for about 30 seconds to 1 minute, the secondary sand blasting process is performed about twice of the primary sand blasting processing time, i.e., about 1 to 2 minutes. For this reason, the bioinert grinding particles such as alumina particles can be completely removed, although depending on conditions of the sand blasting processes.

The material of the particles used in the secondary sand blasting process is desirably sintered substances of hydroxylapatite, α-tricalcium phosphate, β-tricalcium phosphate, tetra-calcium phosphate or the like, a single substance of amorphous calcium phosphate, monetite, brushite, 45S4 glass, other bioactive glass or the like, or these mixtures.

Because sintered calcium phosphate ceramic particles are soft compared with a grit of alumina or glass which are used in usual sand blasting processes to metal, it is desirable that the blasting pressure is set to a slightly higher value than the usual sand blasting processes when the sintered calcium phosphate ceramic particles or the like are used.

Considering the remaining effect of the secondary sand blasting process particles such as calcium phosphate ceramics and so on, the material of the particles is desirably α-tricalcium phosphate, β-tricalcium phosphate, or bioactive glass such as 45S5 glass which have osteo-conduction and are completely absorbed in a living body. However, because it is relatively difficult to form hard particles from a single phase of them, it could be considered that the primary sand blasting process is performed, eutictic particles with hydroxylapatite are formed, or mixture particles with hydroxylapatite are formed.

It should be noted that the above alumina ceramic particles and α-tricalcium phosphate ceramic particles can be chosen in size to have various diameters, for example, of about 0.1 to 0.5 mm in case of the primary sand blasting process, and about 0.01 to 0.1 mm in case of the secondary sand blasting process.

Referring to FIG. 11, in a next step S8, hydrothermal processing is performed to the original implant 1 which is subjected to the secondary sand blasting process. The hydrothermal processing is performed in α-tricalcium phosphate suspension in the temperature of 130° C. for 60 hours such that the titanium surface of the original implant 1 is converted into a titanium oxide surface. On the other hand, in the portion where the secondary α-tricalcium phosphate ceramic particles remain, the surfaces of the particles are converted into hydroxylapatite layers. In this manner, a dentistry implant is obtained in which metal allergy is extremely suppressed and which has the surface of a high bio-compatibility. It should be noted that the temperature and time of the above hydrothermal processing can be selected suitably in accordance with the condition.

Various kinds of pseudo-humor such as Hank's balanced salt solution, various kinds of suspension or saturated solution of calcium phosphate, and mixture solution of them can be used for the hydrothermal processing. Different titanium oxide layers are formed on the surface of the original implant depending upon the processing temperature, the processing time and the kind of solution. However, it is preferable that the processing temperature is in a range of about 60 to 200° C. and the processing time is in a range of about 24 Hr to 48 Hr. The calcium phosphate ceramic particles and so on which have been remained on the surface of the original implant in the blasting process are converted into the hydroxylapatite in the whole particles or the surfaces under these process conditions. As a result, they become stable calcium phosphate ceramics.

Referring to FIG. 11 again, in a next step S10, the thirdly sand blasting process is performed with a low blasting pressure in a range of about 0.2 to 0.3 Pa. As a result, on the surface of the original implant which is subjected to the secondary sand blasting process or the hydrothermal processing in addition to it, the thirdly sand blasting particles formed of, for example, α-tricalcium phosphate, α-tricalcium phosphate, and bioactive glass and so on which have high osteo-conduction.

Next, specific examples 1 to 3 of the present invention will be described. However, the present invention is not limited to these examples.

<EXAMPLE 1>

Figure 12:
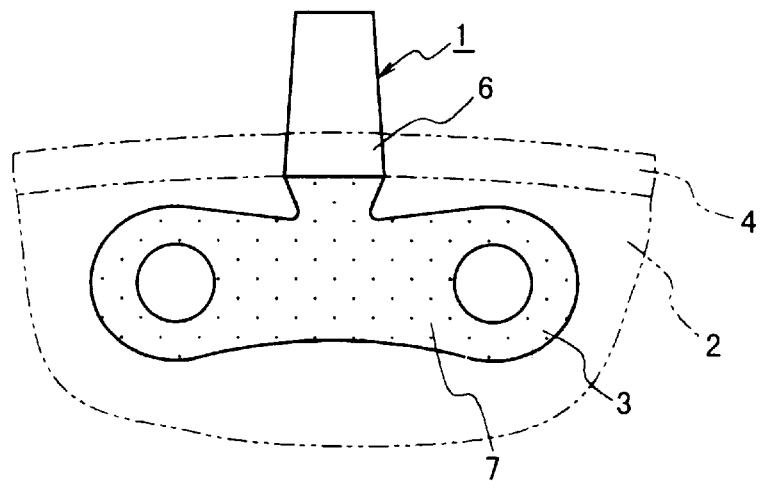
FIG. 12 is a schematic front view of a blade-type implant when the manufacturing method is applied to the blade-type implant.

Only the secondary sand blasting process is performed to the embedded section 3 of the blade-shaped original implant 1 of titanium with the blasting pressure of 0.7 Pa using 45S5 glass particles with an average grain diameter of 0.1 mm. By this, as shown in FIG. 12, the blade-shaped implant formed of titanium is obtained to have an initial osteo-conduction, to have suitable surface roughness for bone, and contain a little amount of 45S5 glass 7. In this case, the gingiva penetrating section 5 and the crowned section 6 are masked such that the blasting particles do not hit. However, the secondary sand blasting process may be performed to the gingiva penetrating section 5 and the crowned section 6. In this example, the original implant is not rotated. However, it may be rotated during the sand blasting process as described above.

<EXAMPLE 2>

Figure 13:
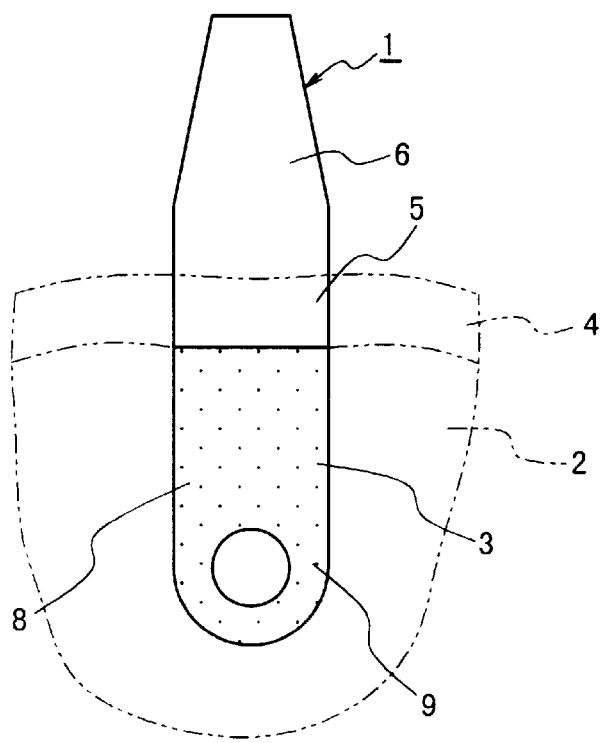
FIG. 13 is a schematic front view of a dentistry implant when the manufacturing method is applied to the dentistry implant.

A titanium implant original implant 1 of a cylindrical shape with the diameter of 4 mm is rotated with the rotation speed of 100 rpm. The primary sand blasting process is performed to the embedded section 3 with the blasting pressure of 0.4 Pa using alumina ceramic particles with an average grain diameter of 0.2 mm. In this case, the gingiva penetrating section 5 and the crowned section 6 is masked such that the alumina ceramic blasting particles do not hit the sections. After ultrasonic cleaning and drying, the secondary sand blasting process is performed with the blasting pressure of 0.7 Pa using the mixture particles in which 45S5 glass particles, β-tricalcium phosphate ceramic particles and sintered hydroxylapatite ceramic particles are mixed with the ratio of 1:1:1 and which have the average grain diameter of 0.05 mm. Thus, as shown in FIG. 13, the final implant formed of titanium is obtained which has the surface 8 of a suitable surface roughness to bone. The final implant has an osteo-conduction, and contains bioactive glass particles and calcium phosphate ceramic particles 9 remained on the surface and finally completely absorbed into the living body.

<EXAMPLE 3>

The primary sand blasting process is performed to the embedded section of a blade implant formed of alloy of titanium and nickel with the blasting pressure of 0.4 Pa, using alumina ceramic particles with the average grain diameter of 0.2 mm. In this case, the gingiva penetrating section 5 and the crowned section 6 are masked such that the blasting particles do not hit the masked sections.

After ultrasonic cleaning and drying, the secondary sand blasting process is performed with the blasting pressure of 0.7 Pa using α-tricalcium phosphate ceramic particles 10 having the average grain diameter of 0.05 mm. After that, a hydrothermal process is performed in α-tricalcium phosphate suspension at the temperature of 130° C. As a result, a titanium oxide film 11 is formed on the titanium surface, and hydroxylapatite layers 12 is formed on the remaining tricalcium phosphate particle surfaces. In this case, some of the tricalcium phosphate particles are converted into hydroxylapatite particles.

Figure 14:
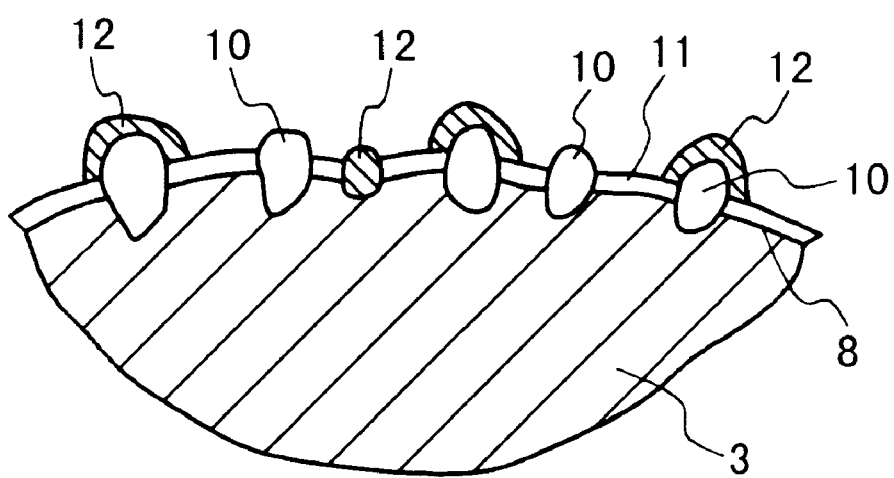
FIG. 14 is a cross sectional view of an implant to which the manufacturing method is applied.

Further, the thirdly sand blasting process is performed with the blasting pressure of 0.3 Pa using α-tricalcium phosphate ceramic particles. As a result, as shown in FIG. 14, the blade implant formed of titanium-nickel alloy is obtained which has a suitable surface roughness to bone. Also, the blade implant has a stable titanium oxide layer formed on the titanium surface, and contains hydroxylapatite of a high bio-compatibility. As a result, α-tricalcium phosphate having an osteo-conduction remains on the surface.

In the present invention, it should be noted that the "bioactive" material implies material to which the living body does not indicate rejection symptoms, which can chemically couple to bone by bio-integration, and which has bio-conduction which is capability of attracting osteoblasts and promoting formation of new bone. The particles used in the present invention have "bio-activity" to realize bio-integration. Therefore, the bioactive particles does not prevent osteo-integration between the implant of titanium and bone but helps realization of the osteo-integration.

Also, in the above embodiments and examples, only the dentistry implant is described. However, the present invention is not limited to them. The present invention can be applied to an implant coupling bones each other, as shown in FIG. 3. In this case, at least one of the sand blasting processes is applied to at least a part of the implant. Specifically, it is desirable for the present invention to be applied to the whole implant.

Further, in the above embodiments and examples, the whole of original implant is formed of titanium or titanium alloy. However, the original implant may be formed of stainless and platinum and only a part of the original implant corresponding to the embedded section may be formed titanium, titanium alloy or titanium oxide in surface or whole. Alternatively, the original implant may be formed to have a calcium phosphate ceramic coating layer in part or whole.

In addition, in the above example, the implant has the crowned section. However, the implant may not have the crowned section as shown in FIGS. 2A and 2B. In this case, an abutment is attached when the implant is inserted.

In the present invention, an implant formed of titanium or titanium alloy is subjected to sand blasting process(es) using particles formed of sintered hydroxylapatite, sintered tricalcium phosphate, or bioactive glass or the mixture of them. The above materials other than the sintered hydroxylapatite are the material absorbed in the bone or substituted by the bone.

These particles stuck into the implant surface through the blasting process prompts formation of new bone around the implant immediately after the implant is embedded in the bone. The material of the particles is gradually absorbed during the formation of new bone, then is completely substituted by the new bone, and finally, the osteo-integration is realized. Thus, the implant is fixed to the bone in the early step after it is embedded in the bone. Also, after the absorption of the material, the implant is provided which is coupled to the bone with stable osteo-integration.

Also, after the primary blasting process is performed to the surface of the original implant formed of titanium or titanium alloy using the particles formed of hard material such as alumina ceramics and silica. As a result, the implant surface has a predetermined surface roughness. The secondary blasting process is performed once again using the blasting particles formed of bioactive glass, or sintered hydroxylapatite, sintered tricalcium phosphate or a mixture of them. In titanium or titanium alloy, i.e., alloy of titanium and material such as nickel, aluminum, vanadium, it is difficult to form a rough surface of titanium or titanium alloy with only the blasting particles of calcium phosphate ceramics and so on. However, by employing the primary sand blasting process, it become possible to efficiently form the rough surface on titanium or titanium alloy surface. In the case of the secondary sand blasting process with the blasting particles of calcium phosphate ceramics and so on, the secondary sand blasting process is performed for a longer time than in the primary sand blasting process, if the particles used in the secondary sand blasting process are smaller than grinding particles used in the primary sand blasting process. As a result, the grinding particles of alumina ceramics and so on can be removed.

Also, the titanium or titanium alloy surface having a rough surface by calcium phosphate ceramics, bioactive glass and so on is subjected to the hydrothermal process at the temperature of about 60 to 200° C. in various types of pseudo-humor and tricalcium phosphate saturation solution or these mixture solution. As a result, a stable layer of the titanium oxide film is provided for the blasted titanium surface. At the same time, a hydroxylapatite layer is formed on the remaining calcium phosphate ceramic blasting particle surface. By this, the thin stable layer mainly formed of titanium oxide on the titanium or titanium alloy surface has a function to promote osteo-integration. At the same time, the surface of the calcium phosphate ceramic particles remained in the titanium or titanium alloy surface becomes a stable hydroxylapatite layer. In this manner, the implant is provided which joins to bone in the earlier step.

Further, the thirdly sand blasting process may be performed to the implant surface, using the particles formed of bioactive glass, sintered hydroxylapatite and tricalcium phosphate, or mixture of them. As a result, the whole surface or bulk is made to have a rough surface. Also, the bioactive particles are stuck into the oxide film layer to allow enough bone formation to be promoted. Such an implant is provided.

As described above, according to the present invention, a portion of titanium or titanium alloy of the implant which contacts bone is subjected to the sand blasting process with particles such as bioactive glass. Instead, the portion of titanium or titanium alloy is subjected to the primary sand blasting process with the hard particles of alumina ceramics and so on and the secondary sand blasting process with the particles of calcium phosphate ceramics and so on. Or, the portion of titanium or titanium alloy is subjected to a hydrothermal process such that the titanium surface is converted into titanium oxide and a calcium phosphate ceramics part is converted into hydroxylapatite. Instead, the sand blasting process is further performed to the titanium oxide surface using secondary blasting material. In this manner, the implant can be obtained to have the titanium surface which contains the particles which contribute to form bone and have a high bio-compatibility. Also, by this method, it is made possible to provide a stable and safe titanium or titanium alloy implant with a low price.

What is claimed is:

1. A method of manufacturing an implant, comprising the steps of:

providing a main body member having bio-compatibility;

dispersedly providing particles formed of material including calcium phosphate at a surface of a proccessed portion of said main body member formed of titanium or titanium alloy such that each of said particles has a part embedded in said processed portion surface and a part protruding from said processed portion surface; and forming a titanium oxide layer on said processed portion surface and a hydroxylapatite layer on a surface of each of said particles.

2. A method according to claim 1, wherein said step of forming a titanium oxide layer includes performing hydrothermal process to said processed portion surface.

3. A method according to claim 2, wherein a solution used in said hydrothermal process is selected from among a group consisting of pseudo-humor, suspension or saturated solution of calcium phosphate, and mixture solution of them.

4. A method according to claim 1, wherein said particles are formed of material selected from among a group consisting of sintered substances of hydroxylapatite, α-tricalcium phosphate, β-tricalcium phosphate, tetra-calcium phosphate, a single substance of amorphous calcium phosphate, monetite, brushite, 45S4 glass, and a mixture of them.

5. A method according to claims 1, further comprising the step of performing a secondary sand blasting process to said processed portion surface using secondary blasting particles formed of bioactive material such that each of said secondary blasting particles has a part embedded in said processed portion surface and a part protruding from said processed portion surface.

6. A method according to claim 5, wherein said secondary blasting particles have osteo-conduction.

7. A method according to claim 6, wherein said secondary blasting particles are formed of material selected from among a group consisting of sintered substances of hydroxylapatite, α-tricalcium phosphate, β-tricalcium phosphate, tetra-calcium phosphate, a single substance of amorphous calcium phosphate, monetite, brushite, 45S4 glass, and a mixture of them.

8. A method according to claim 7, further comprising the step of forming said particles, and wherein said step of forming said particles includes:

producing amorphous calcium phosphate by a precipitate method by adding phosphoric acid solution to calcium hydroxide suspension;

sintering said amorphous calcium phosphate at a predetermined temperature; and crushing said sintered amorphous calcium phosphate to select said sintered hydroxylapatite particles using a mesh.

* * * * *